(12) United States Patent
Yamauchi et al.

(10) Patent No.: US 8,481,254 B2
(45) Date of Patent: Jul. 9, 2013

(54) SUBSTRATE PROBE FOR USE IN MEASURING ENZYME ACTIVITY

(75) Inventors: Fumio Yamauchi, Yokohama (JP); Kimihiro Yoshimura, Yokohama (JP); Katsuaki Kuge, Yokohama (JP); Tetsuya Yano, Tsukuba (JP); Masahiro Shirakawa, Kyoto (JP); Yasuhiro Aoyama, Kyotanabe (JP); Shinsuke Sando, Fukuoka (JP)

(73) Assignee: Canon Kabushiki Kaisha, Tokyo (JP)

( * ) Notice: Subject to any disclaimer, the term of this patent is extended or adjusted under 35 U.S.C. 154(b) by 233 days.

(21) Appl. No.: 12/675,511

(22) PCT Filed: Sep. 8, 2008

(86) PCT No.: PCT/JP2008/066510
§ 371 (c)(1),
(2), (4) Date: May 14, 2010

(87) PCT Pub. No.: WO2009/031717
PCT Pub. Date: Mar. 12, 2009

(65) Prior Publication Data
US 2010/0248279 A1  Sep. 30, 2010

(30) Foreign Application Priority Data

Sep. 7, 2007  (JP) .................................. 2007-232665
Sep. 5, 2008  (JP) .................................. 2008-228433

(51) Int. Cl.
*C12Q 1/00*  (2006.01)
(52) U.S. Cl.
USPC ............................................................ 435/4
(58) Field of Classification Search
USPC ............................................................ 435/4
See application file for complete search history.

(56) References Cited

U.S. PATENT DOCUMENTS

| 6,027,941 | A | * | 2/2000 | Jarvie et al. ................... 436/173 |
| 6,083,486 | A | | 7/2000 | Weissleder et al. |
| 6,592,847 | B1 | | 7/2003 | Weissleder et al. |
| 2003/0073075 | A1 | | 4/2003 | Kawai et al. |

FOREIGN PATENT DOCUMENTS

| JP | 2000-290291 A | 10/2000 |
| JP | 2002-514610 A | 5/2002 |
| WO | 98/57578 A1 | 12/1998 |
| WO | 2006/011810 A2 | 2/2006 |
| WO | WO 2006/011810 | * 2/2006 |

OTHER PUBLICATIONS

Albers M. et al. A 13C HR-MAS Technique for Studying the Cellular bioenergetics Assocates with Prostate Cancer. Proceedings International Society for Magnetic Resonance in Medicine 13(May 7, 2005), p. 2131.*
Kouno T. et al. Letter to the Editor: 1H, 13C and 15N Resonance Assignments of GABARAP, GABAa Receptor Associated Protein. J of Biomolecular NMR 22(1)97-98, Jan. 2002.*
Rodrigues T. et al. A Fast and Sensitive 1H NMR Method to Measure the Turnover of the H2 Hydrogen of Lactate. Magnetic Resonance in Medicine 54(4)1014-1019, 2005.*
Rex A. Moats et al., "A 'Smart' Magnetic Resonance Imaging Agent that Reports on Specific Enzymatic Activity," 36(7) Angew Chem. Int. Ed. Engl. 726-728 (1997).
Christoph Bremer et al., "In Vivo Molecular Target Assessment of Matrix Metalloproteinase Inhibition," 7(6) Nature Medicine 743-748 (Jun. 2001).
J. Manuel Perez et al., "Magnetic Relaxation Switches Capable of Sensing Molecular Interactions," 20 Nature Biotechnology 816-820 (Jul. 2002).
H. Watanabe et al., "Human Brain Glucose Metabolism Mapping Using Multislice 2D 1H-13C Correlation HSQC Spectroscopy," 43 Magnetic Resonance in Medicine 525-533 (2000).
M.J. Albers et al., "A 13C HR-MAS Technique for Studying the Cellular Bioenergetics Associated with Prostate Cancer," 13 Proc. Intl. Soc. Mag. Reson. Med. 1231 (2005).
Elena I. Deryugina et al., "Matrix Metalloproteinases and Tumor Metastasis," 25 Cancer Metastasis Rev. 9-34 (2006).
Jo Louise Seltzer et al., "Cleavage Specificity of Human Skin Type IV Collagenase (Gelatinase): Identification of Cleavage Sites in Type 1 Gelatin, with Confirmation Using Synthetic Peptides," 265 J. Biol. Chem. 20409-13 (1990).

* cited by examiner

*Primary Examiner* — Ralph Gitomer
(74) *Attorney, Agent, or Firm* — Fitzpatrick, Cella, Harper & Scinto

(57) ABSTRACT

Substrate probe capable of detecting enzyme activity with high accuracy and a method for detecting the enzyme activity by a multi nuclear magnetic resonance method using the substrate probe. Multi-dimensional nuclear magnetic resonance is performed by using a substrate probe, which is used for measuring enzyme activity by a multi-dimensional nuclear magnetic resonance method and characterized by containing a enzyme recognition site that is selectively recognized by an active-state enzyme, as at least one constitutional unit, and a group to which at least three nuclear magnetic resonance active nuclei each having a nuclear spin and a different resonance frequency are connected, being present specifically to the enzyme recognition, thereby detecting presence of the substrate probe and the enzyme activity. Alternatively, imaging of the enzyme activity is performed by a multi-dimensional nuclear resonance imaging method.

13 Claims, 10 Drawing Sheets

(A)

SUBSTRATE PROBE FOR USE IN MEASURING ENZYME ACTIVITY

This application is a National Stage application filed under Rule 371 based upon PCT/JP2008/066510 filed Sep. 8, 2008.

TECHNICAL FIELD

The present invention relates to a substrate probe for measuring enzyme activity. The present invention also relates to a method for measuring enzyme activity by a multi-dimensional nuclear magnetic resonance method using the probe and a method for imaging enzyme activity by multi-dimensional nuclear magnetic resonance imaging.

BACKGROUND ART

Enzymes are important proteins which catalyze chemical reactions in a living body. The localization and activities thereof are strictly controlled. It has been found that the localization of enzyme changes and abnormal increase or decrease of enzyme activity occurs in the tissues and cells affected by various diseases.

In tumor cells, the glycolysis using glucose as a raw material plays an important role in producing energy. Particularly in tumor cells present in a low-oxygen environment, the glycolysis acts as a major energy supply source. In the glycolysis, various enzymes act. For example, lactic dehydrogenase is the enzyme which acts in the final stage of the anaerobic glycolysis and converts pyruvic acid to lactic acid. Monitoring (metabolism mapping) the enzyme activity in the glycolysis is desired as a mean for enabling early detection of a solid tumor present in a low-oxygen environment.

A proteolytic enzyme, protease, is a general term used to refer to an enzyme catalyzing hydrolysis of a peptide bond. In a living body, a protease digests a protein into amino acids serving as a nutrient source and decomposes unnecessary proteins in cells. A protease has extremely large physiological significance.

Matrix metalloprotease (MMP) is an enzyme playing a major role in an abnormal site such as a disease site represented by a tumor. MMP catalyzes a decomposition process of extracellular matrix, which is required for local growth and metastasis/infiltration of a tumor (Deryugina E I et al., Cancer Metastasis Rev. v25, 9-34. (2006)). The extracellular matrix consists of substances supporting cells in vivo, such as collagen, elastin, proteoglycan, glycosaminoglycan, fibronectin, laminine and vitronectin. In a tumor site, expression of a plurality of types of MMPs is placed under temporal-spatial control. Most of them are known to be highly expressed. Also, MMP expression increases during metastasis/infiltration of a tumor. For these reasons, the MMP family has been expected to work as a tumor marker and an effective target in developing anticancer agents.

It is extremely important and efficient to monitor the activity of an enzyme such as MMP, which is closely associated with a disease, in the fields of medical/biological studies, clinical test and internal diagnostic imaging. To monitor enzyme activity with high sensitivity and high accuracy, it is necessary to develop probe molecules for monitoring enzyme activity with high sensitivity and a method for detecting the probes.

Probes to be used in-vivo and in-vitro for detecting the activities of enzymes such as a protease have been disclosed in documents. In a method generally employed, a substrate to a degrading enzyme is labeled with a chromophore or a luminophore. After the substrate is cleaved by the degrading enzyme, color or luminescence is generated, which is measured to detect enzyme activity. In the field of diagnostic imaging, reports have been made of a nuclear MRI (magnetic resonance imaging) probe using gadolinium for detecting β-galactosidase activity (e.g., Moats R A et al., Angew Chem. Int. Ed. Engl., v36, 726-728 (1997)), a fluorescent probe using a near-infrared fluorescent dye for detecting protease activity (e.g., Japanese Patent Application Laid-Open No. 2002-514610 and Bremer C et al., Nature medicine, v7, 743-748 (2001)) and an MRI probe using magnetic nano particles for detecting an enzyme activity (e.g., Perez J M et al., Nature Biotechnology, v20, 816-820 (2002)).

These conventional techniques have the following problems that have remained unsolved. First, when an MRI probe is used, degree of relaxation caused by enzymatic activation is relatively low. As a result, it cannot be clearly distinguished that degree of relaxation is observed or that the concentration of probes is observed. When a luminescent probe or a fluorescent probe is used, it is difficult to capture a signal sent from deep part of a living body since permeability of light through the living body is low and light is scattered in the living body. Another problem resides in the specificity of a probe to a substrate, which decreases due to chemical modification and labeling. In addition, a probe has low biocompatibility. Consequently, the dose of the probe comes to be limited, with the result that a signal/noise ratio decreases when enzyme activity is monitored. A substrate probe and a method for detecting enzyme activity that solve these problems have not yet been found.

In the meantime, in order to determine the distribution and structure of a substance of interest in a living body with the lapse of time, NMR (nuclear magnetic resonance) detection using a stable isotope-labeled compound has been employed (see Japanese Patent Application Laid-Open No. 2000-290291 and Watanabe H et al., Magnetic Resonance in Medicine v43, 525-533 (2000)). In Japanese Patent Application Laid-Open No. 2000-290291, an oligonucleotide labeled with $^{13}C$ and $^{15}N$ is detected in a body composition. In Watanabe H et al., Magnetic Resonance in Medicine v43, 525-533 (2000), metabolism mapping of $^{13}C$ glucose administered to a living body is made. However, up to present, detection of protease activity by a multi-dimensional (three dimensional or more) nuclear magnetic resonance method using a stable-isotope labeled substrate probe has not yet been made and a substrate probe to be used in the method has not been disclosed, either.

DISCLOSURE OF THE INVENTION

To enhance the reliability of enzyme detection, the enzyme activity is preferably detected in a system in which the presence of a substrate probe for measuring enzyme activity can be detected and further enzyme activity can be monitored. Furthermore, it is desirable, in view of practice, to use a highly biocompatible probe and a low-invasive detection system.

In these circumstances, the present invention is directed to provide a novel substrate probe and a method for detecting enzyme activity by a multi-dimensional nuclear magnetic resonance method using the probe.

The present inventors found that the activity of a small amount of enzyme can be detected easily with high sensitivity by employing multi-dimensional nuclear magnetic resonance methods using a substrate probe having a stable isotope(s) labeled at an enzyme recognition site, in combination. Based on the finding, the present invention was accomplished.

A first aspect of the present invention is a substrate probe for use in measuring enzyme activity by using a multi-dimensional nuclear magnetic resonance method, wherein the probe has an enzyme recognition site, which is selectively recognized by an active-state enzyme, as at least one constitutional unit, and wherein a group to which at least three nuclear magnetic resonance active nuclei each having a nuclear spin and a different resonance frequency are connected, is present specifically to the enzyme recognition site.

A second aspect of the present invention is the above substrate probe, wherein the nuclear magnetic resonance active nuclei each having a nuclear spin and being present specifically to the enzyme recognition site are artificially enriched.

A third aspect of the present invention is the above substrate probe, wherein the nuclear magnetic resonance active nuclei each having a nuclear spin and being present specifically to the enzyme recognition site are selected from $^1H$, $^{13}C$ and $^{15}N$.

A fourth aspect of the present invention is the above substrate probe, wherein carbon at the 2-position and carbon at the 3-position of pyruvic acid or a salt thereof are labeled with $^{13}C$.

A fifth aspect of the present invention is the above substrate probe, wherein all carbons of glucose are labeled with $^{13}C$ and 7 hydrogen atoms of the 1 to 6 positions thereof are all deuterated.

A sixth aspect of the present invention is the above substrate probe, wherein the enzyme is a glycolytic enzyme.

A seventh aspect of the present invention is the above substrate probe, wherein the glycolytic enzyme is lactic dehydrogenase.

An eighth aspect of the present invention is a method of measuring enzyme activity by the substrate probe based on a multi-dimensional nuclear magnetic resonance method, wherein a change of a multi-dimensional nuclear magnetic resonance signal is measured, and wherein the change is caused by recognition of the substrate probe by an active-state enzyme and a chemical reaction proceeding thereafter.

A ninth aspect of the present invention is the above method of measuring enzyme activity, wherein the nuclear magnetic resonance method at least comprises obtaining nuclear magnetic resonance signals by using the pulse systems of a two-dimensional nuclear magnetic resonance method and a three-dimensional nuclear magnetic resonance method and performing analysis by using the signals in combination.

A tenth aspect of the present invention is the above method of measuring enzyme activity, wherein an amount of the substrate probe and activity of the enzyme are measured by detecting presence of the substrate probe based on a two-dimensional nuclear magnetic resonance signal and detecting the substrate probe reacted with the enzyme based on a three-dimensional nuclear magnetic resonance signal, respectively.

An eleventh aspect of the present invention is an imaging method of enzyme activity based on multi-dimensional nuclear magnetic imaging by the probe, wherein a change of a multi-dimensional nuclear magnetic resonance signal is measured, and wherein the change is caused by recognition of the substrate probe by an active-state enzyme and a chemical reaction proceeding thereafter.

A twelfth aspect of the present invention is the above imaging method of enzyme activity, wherein the nuclear magnetic resonance imaging method comprises obtaining nuclear magnetic resonance signals by using the pulse systems of a two-dimensional nuclear magnetic resonance method and a three-dimensional nuclear magnetic resonance method and performing analysis by using the signals in combination.

A thirteenth aspect of the present invention is the above imaging method of enzyme activity, wherein an amount of the substrate probe and activity of the enzyme are measured by detecting presence of the substrate probe based on a two-dimensional nuclear magnetic resonance signal and detecting the substrate probe reacted with the enzyme based on a three-dimensional nuclear magnetic resonance signal, respectively.

A fourteenth aspect of the present invention is a substrate probe for nuclear magnetic resonance imaging comprising the above substrate probe, for detecting abnormal enzyme activity involved in a disease.

A fifteenth aspect of the present invention is a nuclear magnetic resonance imaging method using the above substrate probe, for detecting abnormal enzyme activity involved in a disease.

A sixteenth aspect of the present invention is the above substrate probe, for detecting a glycolytic metabolite, lactic acid.

A seventeenth aspect of the present invention is a substrate peptide-probe for use in measuring protease activity by a multi-dimensional nuclear magnetic resonance method wherein the probe comprising a protease cleavage site as at least one constitutional unit wherein the protease cleavage site is selectively recognized and cleaved by an active-state protease and a group to which at least three nuclear magnetic resonance active nuclei each having a nuclear spin and a different resonance frequency are connected, is present specifically to the protease cleavage site.

An eighteenth aspect of the present invention is a method for measuring protease activity by using a multi-dimensional nuclear magnetic resonance method employing the substrate peptide-probe wherein a change of a multi-dimensional nuclear magnetic resonance signal, which is caused by cleaving the substrate peptide-probe with an active-state protease, is measured.

A nineteenth aspect of the present invention is an imaging method for protease activity by multi-dimensional nuclear magnetic resonance imaging using the substrate probe, wherein a change of a multi-dimensional nuclear magnetic resonance signal, which is caused by cleaving the substrate probe with an active-state protease, is measured.

A twentieth aspect of the present invention is a substrate probe for use in nuclear magnetic resonance imaging, comprising the substrate peptide-probe and used for detecting abnormal protease activity involved in a disease.

A twenty-first aspect of the present invention is a nuclear magnetic resonance imaging method using the substrate peptide-probe, for detecting abnormal protease activity involved in a disease.

A twenty-second aspect of the present invention is a substrate probe for use in measuring enzyme activity by using a multi-dimensional nuclear magnetic resonance method, wherein the probe has an enzyme recognition site, which is selectively recognized by an active-state enzyme, as at least one constitutional unit, and wherein a group to which at least three nuclear magnetic resonance active nuclei each having a nuclear spin and a different resonance frequency are connected, appears by the enzyme reaction.

A twenty-third aspect of the present invention is a method of measuring enzyme activity by the substrate probe of the twenty-second aspect of the present invention, wherein a change of a multi-dimensional nuclear magnetic resonance signal is measured, and wherein the change is caused by recognition of the substrate probe by an active-state enzyme and a chemical reaction proceeding thereafter.

A twenty-forth of the present invention is an imaging method of enzyme activity based on multi-dimensional nuclear magnetic imaging by the substrate probe of the twenty-second aspect of the present invention, wherein a change of a multi-dimensional nuclear magnetic resonance signal is measured, and wherein the change is caused by recognition of the substrate probe by an active-state enzyme and a chemical reaction proceeding thereafter.

A twenty-fifth of the present invention is a substrate probe for nuclear magnetic resonance imaging comprising the substrate probe of the twenty-second aspect of the present invention for detecting abnormal enzyme activity involved in a disease.

A twenty-sixth of the present invention is a nuclear magnetic resonance imaging method using the substrate probe of the twenty-second aspect of the present invention for detecting abnormal enzyme activity involved in a disease.

The substrate probe for measuring activity of an enzyme according to the present invention contains a site selectively recognized by enzyme. In addition, at least three NMR active nuclei, each having a nuclear spin and a different resonance frequency, are connected specifically to the recognition site. Therefore, the probe alone can be selectively observed by a multi nuclear magnetic resonance method. As a result, enzyme activity can be detected with high sensitivity. Furthermore, since the probe has a high biocompatibility, enzyme can be specifically analyzed by multiple-dimensional nuclear resonance imaging with respect to not only its in-vivo activity but also positional information thereof.

According to the present invention, there can be provided a novel and highly biocompatible substrate probe for measuring enzyme activity, a method for detecting enzyme activity with a high signal/noise ratio by using the probe, and an imaging method for the enzyme activity.

Further features of the present invention will become apparent from the following description of exemplary embodiments with reference to the attached drawings.

BEST MODES FOR CARRYING OUT THE INVENTION

Figure 1:
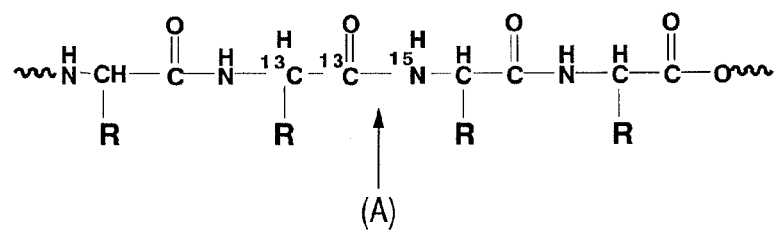
FIG. 1 schematically illustrates the structural formula of the substrate peptide-probe provided by the present invention (R represents a side-chain moiety of each amino acid).

The substrate probe for measuring enzyme activity of the embodiment is a compound containing a site recognized by an enzyme (hereinafter, referred to as a "recognition site"). More specifically, the substrate probe of the present invention has a site or domain as a constitutional unit which is specifically recognized by an enzyme and a portion thereof is chemically altered. The phrase "as a constitutional unit" means that a substrate probe has one or more recognition site. The substrate probe of the present invention may have a plurality of recognition sites. In the embodiments of the present invention, a group having at least three nuclear magnetic resonance active nuclei (NMR nuclei), each having a nuclear spin and a different resonance frequency, is connected specifically to the recognition site. Note that the phrase "connected specifically to the recognition site" used in the present invention means that the group is specifically connected to a functional site, which causes a change before and after enzyme reaction, for example, causes resonance or not, or causes a shift of a resonance frequency.

In the present invention, the "enzyme" refers to a protein catalyzing an enzymatic reaction. Examples of the enzyme may include an oxidation-reduction enzyme, transferase, hydrolytic enzyme, lyase, isomerase and ligase.

In the present invention, the substrate of an enzyme (sometimes referred simply to as a "substrate") is a substance upon which the enzyme acts. Examples of the substrate may include low molecular compounds, high molecular compounds, amino acids, peptides, proteins, nucleic acids and polynucleotides. More specific examples thereof may include a protease-recognizing peptide, pyruvic acid, acetylcholine, choline ester, choline and glucose.

As a substrate probe for use in measuring enzyme activity to be provided by the present invention, a substrate to an enzyme involved in the anaerobic glycolytic metabolism of a cell can be used. In the anaerobic glycolytic metabolism, ATP is provided from glucose to produce lactic acid and alanine. It is known that the anaerobic glycolytic metabolism is accelerated in a tumor tissue and uptake of glucose and generation of lactic acid are activated. Examples of the enzyme involved in the glycolytic metabolism may include hexokinase, glucosephosphate isomerase, phosphofructokinase, aldolase, triosephosphate isomerase, glyceraldehyde-3-phosphate dehydrogenase, phosphoglycerate kinase, phosphoglyceromutase, enolase, pyruvate kinase and lactic dehydrogenase. The state of glycolytic metabolism can be monitored by detecting the activities of these enzymes, leading to detection of a tumor tissue in which the glycolytic metabolism is accelerated.

To detect the activity of lactic dehydrogenase, pyruvic acid or its salt labeled with an isotope and represented by the formula (2) below can be suitably used. The substrate probe is labeled with $^{13}C$ at the 2-position and the 3-position. Lactic dehydrogenase is the enzyme for converting pyruvic acid to lactic acid and can be selectively detected by detecting a multi-dimensional nuclear magnetic resonance signal from methine proton of lactic acid represented by the formula (3) below and produced by a cell to which pyruvic acid labeled with an isotope is administered, as is described in examples of the present invention.

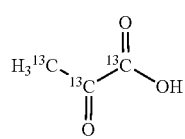
(2)

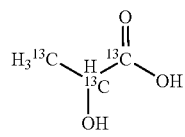
(3)

Furthermore, to detect the total activity of the glycolytic enzymes, in other words, to detect the total activity of the glycolytic metabolism, glucose labeled with a deuterated isotope (D-Glucose-$^{13}C_6$, 1, 2, 3, 4, 5, 6, 6-$d_7$) and represented by the formula (4) below can be suitably used. As shown in formula (4), all carbons of glucose are labeled with $^{13}C$ and 7 hydrogen atoms bind with the carbon at the 1 to 6 positions thereof are all deuterated. As shown in formula (5), the substrate probe is designed to generate a detectable proton when converted to alanine or lactic acid during the glycolytic metabolism reactions. Therefore, a multi-dimensional nuclear magnetic resonance signal from a glycolytic metabolite of glucose, i.e., alanine or lactic acid, can be selectively obtained by use of the substrate probe, meaning that glycolytic metabolism activity can be detected.

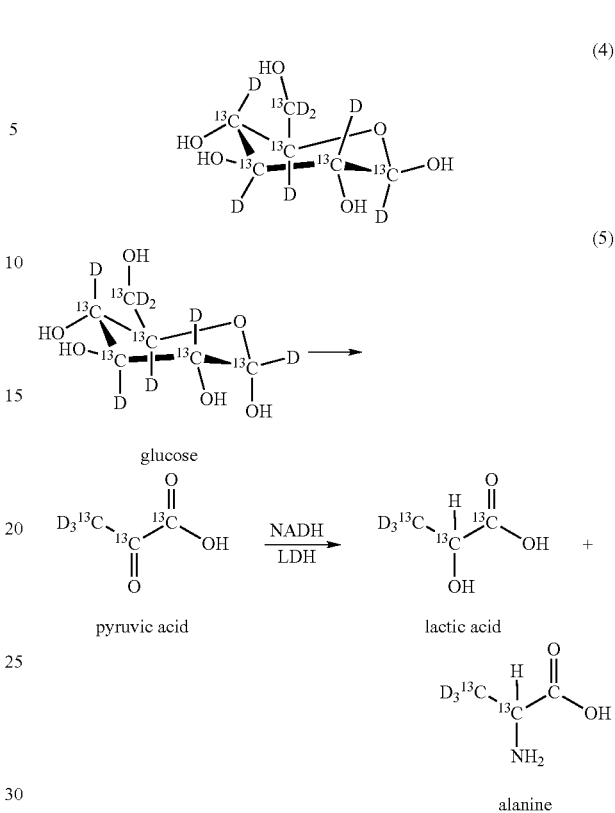

The substrate peptide-probe for measuring protease activity to be provided by the present invention is a peptide containing a protease cleavable site (hereinafter, referred to as a "protease cleavage site"). More specifically, the substrate peptide-probe of the present invention has a site or domain as a constitutional unit having an amino acid sequence which is specifically recognized and cleaved by a protease. The phrase "having a constitutional unit" means that a peptide has one or more protease cleavage sites. The substrate peptide-probe of the present invention may have a plurality of protease cleavage sites. In the embodiments of the present invention, a group having at least three nuclear magnetic resonance active nuclei (NMR nuclei), each having a nuclear spin and a different resonance frequency, is connected specifically to the protease cleavage site. Note that the phrase "specifically to the protease cleavage site" used in the present invention means that the group is specifically connected to a functional site, which causes a change before and after cleavage, for example, causes resonance or not, or causes a shift of a resonance frequency.

The peptide used in the present invention refers to a polypeptide having a plurality of amino acids bonded to each other. Note that a polypeptide having about 30 to 50 amino acids bonded to each other may be sometimes referred to as an oligopeptide. Needless to say, not only an oligopeptide but also a protein falls within the range of the peptide of the present invention. Amino acids generally have L-form. However, the amino acids except for that of a protease recognition sequence may have D-form or may be non-natural amino acids.

More specifically, a protease cleavage site of a substrate peptide-probe according to the present invention refers to a site having an amino acid sequence specifically recognized by a protease, more specifically, a site having an amino acid sequence specifically recognized and hydrolyzed by an active-state protease. The protease cleavage site is generally a site or domain having about 2 to 20 amino acid residues, generally 3 to 20 and sometimes 4 or 5 to 15 amino acid residues.

The activity of a protease that can be measured in the present invention is not particularly limited as long as its substrate is a peptide. Protease is a general term used to refer to an enzyme catalyzing hydrolysis of a peptide bond and plays a wide variety of roles associated with biophylaxis, activity regulation, nutrition absorption, degradation of a protein and reuse thereof. As the substrate probe, any amino acid sequence may be selected depending upon the target protease to be detected. For example, as the target protease, a matrix metalloprotease (MMP) is suitable. When matrix mettaloprotease 2 (MMP2) is selected from the group of matrix metalloproteases (MMP) and subjected to detection, an amino acid sequence, GPLGVRGK, can be used (Bremer C et al., Nature medicine, v7, 743-748 (2001) and Seltzer J L et al., The Journal of Biological Chemistry v265, 20409-20413 (1990)). Such a substrate peptide-probe can be produced by a general peptide synthesis method or a production system using a microorganisms or cultured cells.

Examples of the NMR active nuclei to be used in the present invention and having different resonance frequencies may include stable isotopes such as $^1H$, $^{13}C$, $^{15}N$, $^{17}O$, $^{19}F$, $^{31}P$ and $^{29}Si$. Of them, $^1H$ is preferably used in combination with any one of $^{13}C$ (naturally occurring ratio: 1.1%), $^{15}N$ (naturally occurring ratio: 0.366%) and $^{17}O$ (naturally occurring ratio: 0.038%). In addition, in view of measurement sensitivity, $^1H$ is preferably used in combination with $^{13}C$ or $^{15}N$.

A substrate probe having NMR active nuclei whose ratios are artificially enriched compared to the naturally-occurring ratio by replacing (labeling) a carbon atom and nitrogen atom of the molecular skeleton by the aforementioned NMR active nuclei such that at least three NMR active nuclei are connected specifically to the recognition site of the substrate probe. A substrate peptide-probe having NMR active nuclei whose ratios are artificially enriched compared to the naturally-occurring ratio by replacing (labeling) a carbon atom and nitrogen atom of an amino acid skeleton by the aforementioned NMR active nuclei such that at least three NMR active nuclei are connected specifically to the cleavage site of the substrate peptide-probe. Note that the "artificially enriched" used in the present invention means that NMR active nuclei are introduced to increase the ratios thereof than the naturally-occurring ratios. This includes artificial synthesis of a substrate probe using NMR active nuclei. In the present invention, a substrate probe having NMR active nuclei specifically at an enzyme recognition site whose ratios are artificially enriched has "isotopic reagent comprising a site which is recognized selectively by an active-state enzyme (an enzyme recognition site) as at least one constitutional unit, and having a group to which at least three nuclear magnetic resonance active nuclei each having a nuclear spin and a different resonance frequency at the above enzyme recognition site" at higher ratio compared to the natural abundance. When these labels are introduced in a substrate, the molecular weight of the substrate changes extremely slightly. However, the chemical and physical properties of the molecule hardly change. Therefore, the substrate probe of the present invention can be regarded as being identical to a naturally-occurring substrate. In this respect, the substrate probe of the present invention has an advantage over a conventional probe for use in measuring enzyme activity. Thus, a burden given by the substrate probe of the present invention on a living body can be reduced and good specificity of the probe to an enzyme can be maintained.

The method for detecting enzyme activity of the present invention is characterized by bringing a substrate probe into contact with a target enzyme and thereafter measuring multidimensional nuclear magnetic resonance caused by magnetization transfer of the NMR active nuclei such as stable isotopes introduced therein, more preferably, measuring it by a two-dimensional nuclear magnetic resonance method (two-dimensional resonance NMR method) in combination with a three-dimensional nuclear magnetic resonance method (three-dimensional resonance NMR method).

The substrate probe to be provided by the present invention has a structure in which at least three NMR active nuclei (NMR active nuclei of mutually different types) different in resonance frequency are sequentially connected specifically to an enzyme recognition site. Since a structure in which at least three NMR active nuclei are sequentially connected is present specifically to the recognition site, a nuclear magnetic resonance signal, which reflects the presence or absence of recognition and reaction of a probe, can be detected. In short, the substrate probe of the present invention serves as a substrate probe for nuclear magnetic resonance. The substrate probe of the present invention has preferably a sequence of $^1H$—$^{15}N$—$^{13}C$, $^1H$—$^{13}C$—$^{13}C$ or $^1H$—$^{13}C$—$^{15}N$ present in the molecular skeleton of the probe. As long as such a sequence is present, three-dimensional resonance can occur by magnetization transfer between three nuclei. As a result, a nuclear magnetic resonance signal derived from the substrate probe can be selectively detected. Even in the case where two of $^{13}C$s are present next to each other as is in the case of $^1H$—$^{13}C$—$^{13}C$, the resonance frequencies of these $^{13}C$s mutually vary as long as the groups connected to adjacent $^{13}C$s mutually differ. Therefore, these $^{13}C$s are regarded as mutually different nuclei. In these sequences, two-dimensional nuclear resonance can be measured in the same manner as in magnetization transfer between two nuclei such as $^1H$—$^{15}N$ and $^1H$—$^{13}C$.

To describe more specifically, the nuclear magnetic resonance signal of a substrate peptide-probe is excited by a magnetic resonance apparatus capable of performing simultaneous excitation. Then, the magnetic resonance signal is caused by magnetization transfer between nuclei. And then, information of a second nucleus ($^{13}C$ or $^{15}N$) and a third nucleus ($^{13}C$ or $^{15}N$) of the isotope-labeled probe, is converted to the magnetic resonance signal of the first nucleus ($^1H$). In this manner, only a probe labeled with isotopes can be selectively detected. Measurement is performed by the multidimensional resonance pulse system, in particular, by using a second-dimensional resonance pulse system in combination with a third-dimensional resonance pulse system. More specifically, presence of a substrate probe and the structure thereof can be observed (detected) by each of the pulse systems.

On the other hand, when an enzyme attacks the site among these three nuclei or its proximity, three-dimensional resonance due to magnetization transfer cannot occur between three nuclei or a nucleic magnetic resonance signal thereof greatly varies. Based on this phenomenon, proteolytic cleavage of a peptide can be detected. For example, when these three nuclei are cleaved between them or in its proximity, three-dimensional resonance due to magnetization transfer cannot occur between three nuclei or a nucleic magnetic resonance signal thereof greatly varies. Based on this phenomenon, proteolytic cleavage of a peptide can be detected. A two-dimensional resonance signal caused by magnetization transfer between two nuclei can be detected regardless of the presence or absence of cleavage by a protease. Therefore, the two-dimensional resonance signal indicates the presence of a probe, and thus, can be used as an internal standard. As another example, a probe wherein three-dimensional resonance appears only after an enzyme reaction and a system detecting such a probe can be used as indicated in the formula (4).

As described above, the present invention is directed to a method for measuring enzyme activity using a multi-dimensional nuclear magnetic resonance of a substrate probe as mentioned above. This method includes a method for measuring enzyme activity using a nuclear magnetic resonance method wherein a change of multi-dimensional nuclear magnetic resonance signal is caused by recognition and reaction of active-state enzyme at the substrate probe. More specifically, the present invention is directed to a method for measuring enzyme activity using a multi-dimensional nuclear magnetic resonance method characterized by having a step of bringing a substrate probe according to the present invention into contact with a enzyme of interest, a step of detecting the presence of the substrate probe based on an NMR signal from the substrate probe by use of two-dimensional nuclear magnetic resonance measurement and a step of detecting enzyme activity based on an NMR signal from the substrate probe by use of three-dimensional nuclear magnetic resonance measurement.

The nuclear magnetic resonance method herein preferably has a step of obtaining each of the nucleic magnetic resonance signals by use of pulse systems of a two-dimensional nuclear magnetic resonance method and a three-dimensional nuclear magnetic resonance method and a step of performing analysis by using these signals in combination. Further, it is also preferable to detect the presence of a substrate probe by a two-dimensional nuclear magnetic resonance signal and detect cleaved products of the substrate probe with an enzyme by use of a three-dimensional nuclear magnetic resonance signal, thereby detecting the amount of the substrate probe present and the activity of the enzyme.

The present invention can further perform imaging of protease activity by multi-dimensional resonance NMR imaging.

To describe more specifically, the nuclear magnetic resonance signal of a substrate probe is excited by a magnetic resonance apparatus capable of performing simultaneous excitation. Then, the magnetic resonance signal is caused by polarization transfer between nuclei. And then, information of a second nucleus ($^{13}C$ or $^{15}N$) and a third nucleus ($^{13}C$ or $^{15}N$) of the isotope-labeled probe, is converted to the magnetic resonance signal of the first nucleus ($^1H$). In this manner, only a probe labeled with isotopes can be selectively detected. In this manner, the enzyme can be selectively detected. Subsequently, the gradient magnetic pulses regarding the x-axis, y-axis and z-axis are simultaneously applied to obtain positional information of the magnetic resonance signal of a first nucleus ($^1H$) derived from the probe. Imaging is performed by using a multidimensional resonance pulse system, in particular, by using a two dimensional resonance NMR method and a three dimensional resonance NMR method in combination. More specifically, the positional and structural information of the substrate probe is obtained by imaging by use of individual pulse systems. The positional, quantitative or structure information of a substrate is indicated by appearance, disappearance or intensity change of NMR signals (two-dimensional resonance NMR signal and three-dimensional resonance NMR signal) derived from a substrate probe. Accordingly, imaging of in-vivo enzyme activity can be performed through time-lapse and quantitative detection of a probe and structural change of a probe.

As described above, the present invention comprises an imaging method of enzyme activity using multi-dimensional nuclear magnetic resonance imaging by a probe as mentioned above, wherein measuring a change of a multi-dimensional nuclear magnetic resonance signal caused by recognition and reaction of active-state enzyme at the substrate probe. More specifically, the present invention comprises an imaging method of an enzyme activity by using a multi-dimensional nuclear magnetic resonance method (that is, an imaging method of an enzyme activity by multi-dimensional resonance MRI), wherein including a step of bringing the substrate probe into contact with an enzyme of interest, a step of detecting the presence of the probe based on the NMR signal of the probe obtained by two-dimensional nuclear magnetic resonance measurement and a step of detecting enzyme activity based on the NMR signal of the probe obtained by three-dimensional nuclear magnetic resonance measurement.

In this method, the nuclear magnetic resonance imaging method preferably has a step of obtaining individual nuclear magnetic resonance signals by using pulse systems of a two-dimensional nuclear magnetic resonance method and a three-dimensional nuclear magnetic resonance method and a step of performing analysis by using these signals in combination. Furthermore, it is preferable to measure the amount of the substrate probe and activity of the enzyme by detecting the presence of a substrate probe based on the two-dimensional nuclear magnetic resonance signal and detecting the substrate which has been processed by the enzyme reaction by the three-dimensional nuclear magnetic resonance signal.

The substrate probe of the present invention can be used in diagnosis of a disease having a correlation with enzyme activity, and can be preferably used in an imaging method of abnormal enzyme activity involved in a disease, based on MRI. A substrate probe for MRI can be applied to a test sample such as cultured cells or tissues for investigation of a disease. Furthermore, to diagnose the state of a patient contracting the disease and make a diagnosis for preventing a healthy person from contracting the disease the substrate probe may be introduced into a living body or the cells or tissues taken from a living body. In this manner, imaging of enzyme activity based on MRI can be performed.

A diagnosis method using the substrate probe of the present invention and based on a nuclear magnetic resonance method has a step of introducing the substrate probe into cultured cells, the cells and tissues taken from a living body or a living body, and a step of detecting abnormal enzyme activity involved in a disease, thereby monitoring the site and state of the disease.

Protease is one of the examples of the enzymes to be detected by the substrate probe of the present invention. The following is the explanation of a substrate peptide-probe which is an example of substrate probes.

FIG. 1 illustrates the general formula of the substrate peptide-probe to be used in the method for detecting protease activity of the present invention, and more specifically, illustrates a preferred embodiment of nuclei labeled with isotopes. In this embodiment, two amino acid residues of the protease cleavage site are labeled. To describe more specifically, the 1-position and 2-position carbon atoms of the skeleton of an amino acid close to the N-terminal are labeled with $^{13}C$ and the nitrogen atom of the skeleton of the amino acid close to the C terminal is labeled with $^{15}N$. In the figure, Rs represent amino acid side-chains that may be mutually different and the arrow represents a protease cleavage site.

Figure 2:
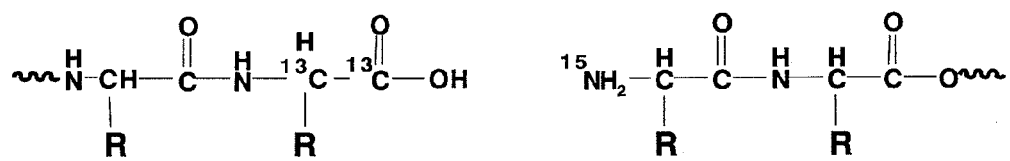
FIG. 2 illustrates the structural formula of the substrate peptide-probe after cleaved by a protease.

FIG. 2 illustrates the state of the substrate peptide-probe illustrated in FIG. 1 after a peptide bond is hydrolyzed by a protease.

Figure 3:
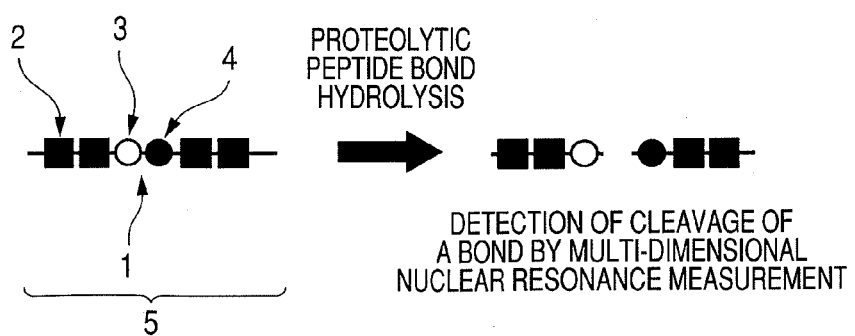
FIG. 3 illustrates a schematic diagram showing the method for detecting protease activity provided by the present invention.

FIG. 3 illustrates a schematic diagram showing the method for detecting protease activity provided by the present invention. When proteolytic peptide-bond hydrolysis occurs, a peptide bond is cleaved at a protease cleavage site indicated as 1. As a result, a substrate peptide-probe 5 is divided into two fragments. One of the amino acids constituting a peptide bond, which constitutes the protease cleavage site 1 of the substrate peptide-probe 5, is designated as a stable isotope labeled amino acid 3. The other amino acid is designated as a stable isotope labeled amino acid or a non-labeled amino acid 4. Subsequently, replacement with corresponding stable isotope is performed such that three NMR active nuclei such as stable isotope labeled amino acids are connected. As a result, the nuclear magnetic resonance signals generated by three-dimensional resonance due to magnetization transfer caused between three nuclei differ before and after cleavage of the peptide bond. Based on the difference, whether a peptide bond is hydrolyzed by a protease or not can be detected.

EXAMPLES

The present invention will be more specifically described by way of examples; however, the scope of the present invention is not limited by the examples. Note that protease will be sometimes simply referred to as the "enzyme".

Example 1

Detection of MMP2 Activity 1-1: Synthesis of Isotope-Labeled Substrate Peptide-Probe to MMP2

(1) Synthesis of Peptide GPLGVRGK (H-Gly-Pro-Leu-Gly-Val-Arg-Gly-Lys-NH$_2$)

Peptide GPLGVRGK (H-Gly-Pro-Leu-Gly-Val-Arg-Gly-Lys-NH$_2$: SEQ ID NO:1) was synthesized by a general Fmoc method. To obtain a peptide having the 4th amino acid (Gly) from the N terminal, labeled with $^{13}$C at carbon atoms of the 1-position and the 2-position of the skeleton thereof and the 5th amino acid (Val) from the N terminal, labeled with $^{15}$N at nitrogen atom of the skeleton thereof, amino acids (Gly and Val) to be placed at these positions were previously labeled with isotopes and subjected to synthesis. Synthesis was performed by using Rink amide resin (manufactured by Novabiochem) in an amount of 0.2 mmol. The isotope-labeled amino acid reagents (L-Valine-$^{15}$N, N-FMOC derivative, GLYCINE-$^{13}$C$_2$, F-MOC derivative) used in synthesis were purchased from ISOTEC. If not otherwise specified, non-isotope labeled amino acids and amino acid synthesis reagents and solvents used in this experiment were purchased from Watanabe Chemical Industries Ltd. The arginine residue used herein had a side-chain protected with a pentamethyldihydrobenzofuran-5-sulfonyl (pdf) group. The lysine residue used herein had a side-chain protected with a t-butoxycarbonyl (Boc) group.

The Fmoc group was deprotected by 20% piperidine in N-methylpyrrolidone (NMP). As a washing solvent, NMP was used. The peptide was synthesized by repeating a coupling reaction using Fmoc-amino acid (3 equivalents), 2-(1H-benzotriazol-1-yl)-1,1,3,3-tetramethyluroniumhexafluorophosphate (HBTU) (3 equivalents) in NMP, 1-hydroxybenzotriazole (HOBt) and diisopropylethylamine (DIEA) (6 equivalents) for 30 minutes. Presence of a free amino group left on the resin after the deprotection and coupling reactions was confirmed by the Kaiser test (see E. Kaiser, et al. (1970) Anal. Biochem., 34, 595). The obtained peptide resin was washed with NMP, dichloromethane (DCM) and methanol, and dried under vacuum.

Removal of the side-chain protecting group from the peptide and dissociation of the peptide from the resin were performed by treating the peptide resin in a trifluoroacetic acid (TFA) containing triisopropyl silane (1%), H$_2$O (5%), thioanisole (5%), ethanedithiol (2.5%) and phenol (5%), at room temperature for 2 hours. The remaining resin was filtrated off by a glass filter. To the filtrate, t-butylmethyl ether was added to precipitate a crude peptide. The precipitate was centrifugally collected, and further washed with t-butylmethyl ether, dried under vacuum and dissolved in 30% acetic acid (1 mL).

Figure 4:
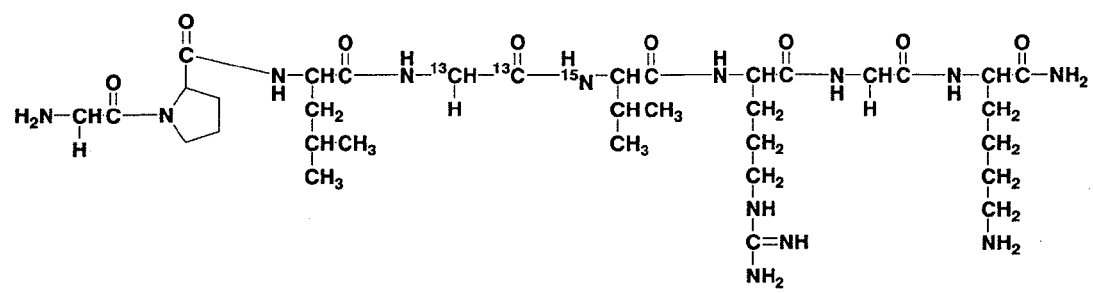
FIG. 4 illustrates the structural formula of a synthesized isotope-labeled peptide GPLGVRGK.

The peptide was analyzed by HPLC (A=H$_2$O/0.1% TFA and C=CH$_3$CN/0.1% TFA: 0 to 25 minutes: 5 to 30% C, using an YMC HPLC column, YMC-Pack ODS-A (AA12S05-2546WT) manufactured by YMC and having a length of 250 mm and an inner diameter of 4.6 mm; a particle diameter of 5 µm, a pore diameter of 12 nm, a flow amount of 0.8 mL/minute; and detection was made at UV of 220 nm) and the major peak emerged at the elution time of 18.6 min. was separated. The mass of the peptide was checked by a MALDI-TOF mass spectrometer. Although a theoretical value M+H$^+$ of an isotope labeled peptide GPLGVRGK was 785.5, an actual measurement value of 785.6 was obtained. The solution separated was lyophilized to obtain purified peptide (amount: 93 mg, yield: 60%). The structural formula of the peptide obtained is illustrated in FIG. 4.

1-2: Reaction Between MMP2 and Substrate Peptide-Probe

A TCNB buffer (50 mM Tris, 10 mM CaCl$_2$, 150 mM NaCl, 0.05% Brij 35, pH 7.5) was used as a buffer for an enzymatic reaction. A MMP2 precursor (R&D systems Inc.) was activated in 1 mM 4-aminophenylmercury acetate (APMA, manufactured by Sigma) in accordance with the protocol attached to the product to obtain activated MMP2 (hereinafter, simply referred to as MMP2). MMP2 (1 µg) was dissolved in 0.9 mL of the reaction buffer. To this solution, 780 µg of the substrate peptide synthesized above was added to obtain a solution containing a peptide in a concentration of 1 mM. The resultant solution was incubated at 25° C. for 18 hours.

The peptide was cleaved by an enzyme, MMP2. The peptide solution before and after the reaction with the enzyme was monitored by HPLC analysis (A=H$_2$O/0.1% TFA and C=CH$_3$CN/0.1% TFA; initial 5 minutes: 0% C, 5 to 35 minutes: 0 to 30% C, using an YMC HPLC column, YMC-Pack ODS-A (AA12S05-2546WT) manufactured by YMC and having a length of 250 mm and an inner diameter of 4.6 mm; a particle diameter of 5 µm, a pore diameter of 12 nm, a flow amount of 0.8 mL/minute; and detection was made at UV of 220 nm). HPLC elution profiles of the peptide solution (MMP−) before treated with the enzyme and the peptide solution (MMP+) after treated with the enzyme are illustrated in FIG. 5.

Figure 5:
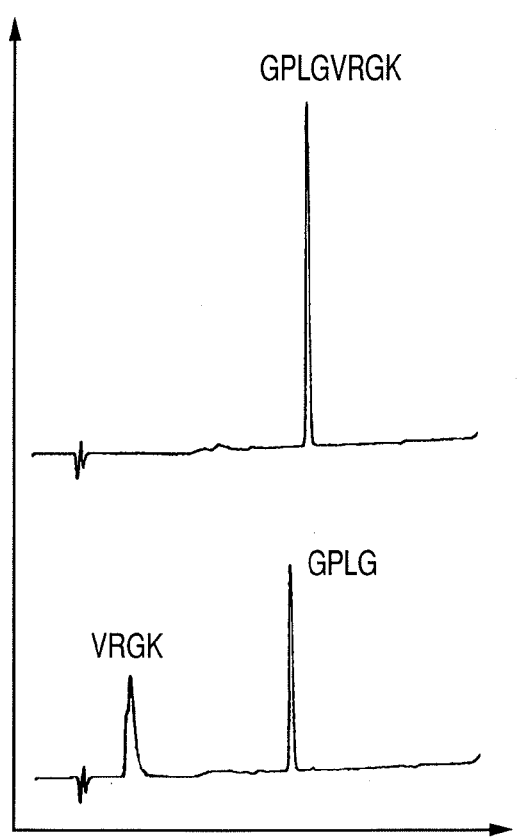
FIG. 5 illustrates HPLC elution profiles before and after the isotope-labeled peptide GPLGVRGK is cleaved by MMP2.

As illustrated in FIG. 5, in the profile (MMP−) before reacted with the enzyme, a single peak was obtained at elution time of 25.8 min. The peak was separated and subjected to MALDI-TOF-MS analysis. Although a theoretical value M+H$^+$ of an isotope labeled peptide GPLGVRGK was 785.5, an actual measurement value of 785.6 was obtained. In the profile (MMP+) after reacted with the enzyme, two peaks emerged (at elution time of 8.9 min. and 24 min.). These peaks were separated and subjected to MALDI-TOF-MS analysis. The value of M+H$^+$ at elution time of 24 min was 345.3. The value of M+H$^+$ at elution time of 8.9 min. was 459.4. After cleaved with MMP2, the peptide GPLGVRGK was divided into a fragment of GPLG (theoretical value of M+H$^+$: 345.2) and a fragment of VRGK (theoretical value of M+H$^+$: 459.3). Therefore, the peak initially emerged at elution time of 8.9 min. was VRGK and the peak lately emerged at elution time of 24 min. was GPLG. From the results above, it was found that the synthesized peptide labeled with isotopes is completely cleaved by MMP2 at room temperature for 18 hours.

1-3: Multi-Dimensional NMR Measurement (Two-Dimensional Resonance, Three-Dimensional Resonance)

The sample of the isotope-labeled peptide thus obtained was subjected to multi-dimensional NMR measurement using an apparatus DRX 700 manufactured by Bruker Corporation, before and after reacted with an enzyme. To each of the samples, 10% heavy water was added. Measurement was performed at 25° C., 2 to 512 times.

Figure 6:
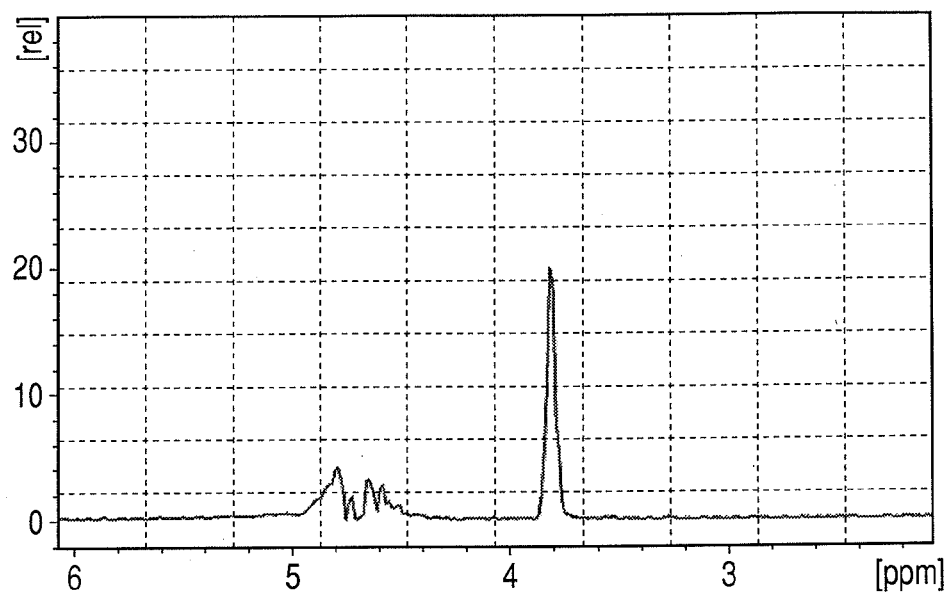
FIG. 6 shows a proton NMR spectrum of $^1H$—$^{13}C$ two-dimensional resonance of the isotope-labeled peptide GPLGVRGK before the peptide is reacted with an enzyme.

FIG. 6 illustrates the proton NMR spectrum of $^1$H-$^{13}$C two-dimensional resonance of the isotope-labeled peptide GPLGVRGK (MMP−) before reacted with an enzyme. The signal of a proton bound to the α-carbon of $^{13}$C-labeled glycine was detected at about 3.8 ppm.

Figure 7:
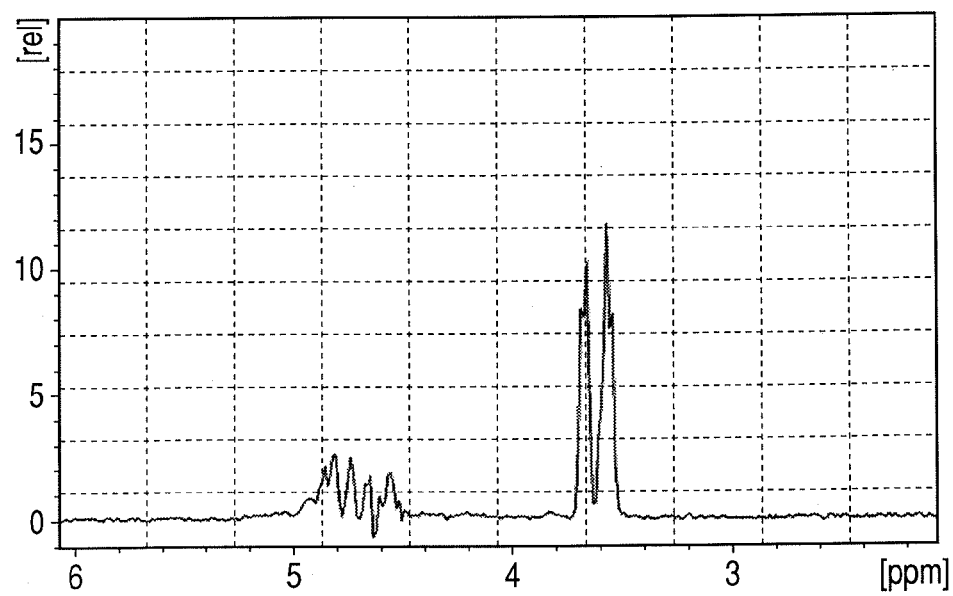
FIG. 7 shows a proton NMR spectrum of $^1H$—$^{13}C$ two-dimensional resonance of the isotope-labeled peptide GPLGVRGK after the peptide is reacted with the enzyme.

On the other hand, FIG. 7 illustrates the proton NMR spectrum of $^1$H—$^{13}$C two-dimensional resonance of the isotope-labeled peptide GPLGVRGK (MMP+) after reacted with the enzyme. The signal of a proton bound to the α-carbon of $^{13}$C-labeled glycine was detected at about 3.6 to 3.7 ppm.

Figure 8:
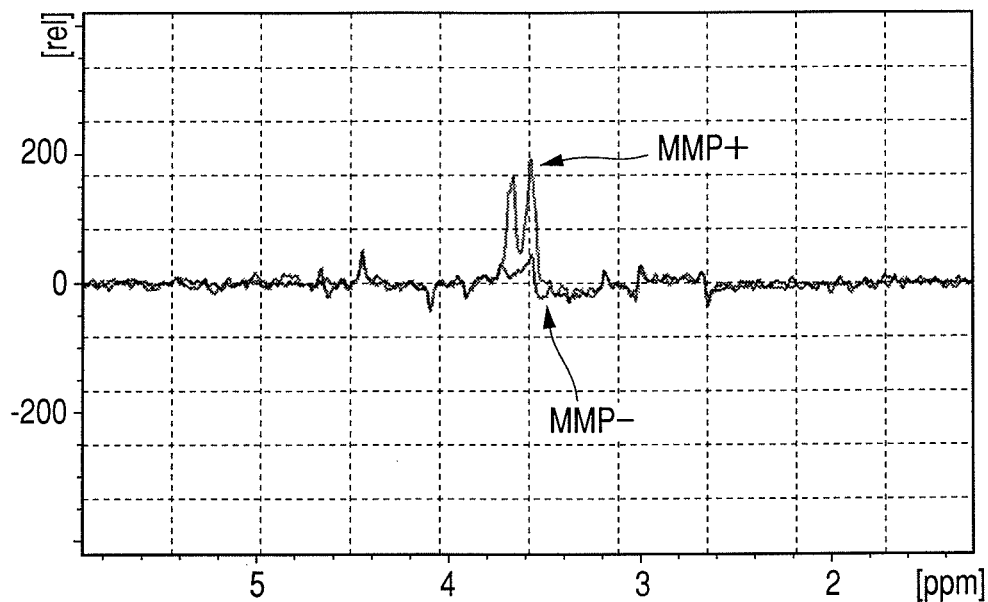
FIG. 8 shows proton NMR spectra of $^1H$—$^{13}C$—$^{13}C$ multi-dimensional resonance of the isotope-labeled peptide GPLGVRGK before the peptide (MMP−) is reacted with an enzyme and after the peptide (MMP+) is reacted with the enzyme.

FIG. 8 illustrates the proton NMR spectra of $^1$H—$^{13}$C—$^{13}$C multi-dimensional resonance of the isotope-labeled peptides (MMP−) and (MMP+) before and after reacted with the enzyme. According to the multi-dimensional resonance NMR observation method, a $^1$H—$^{13}$C—$^{13}$C—$^{15}$N (glycine-valine) bond un-cleaved was not detected but cleaved glycine $^1$H—$^{13}$C—$^{13}$C was selectively observed (in this observation method, $^{15}$N was also irradiated, four dimensional resonance actually occurred). Accordingly, in the spectrum (MMP−) before the enzyme reaction, no signal was detected. However, in the spectrum (MMP+) after the enzyme reaction, a proton signal was observed at about 3.6 to 3.7 ppm.

Figure 9:
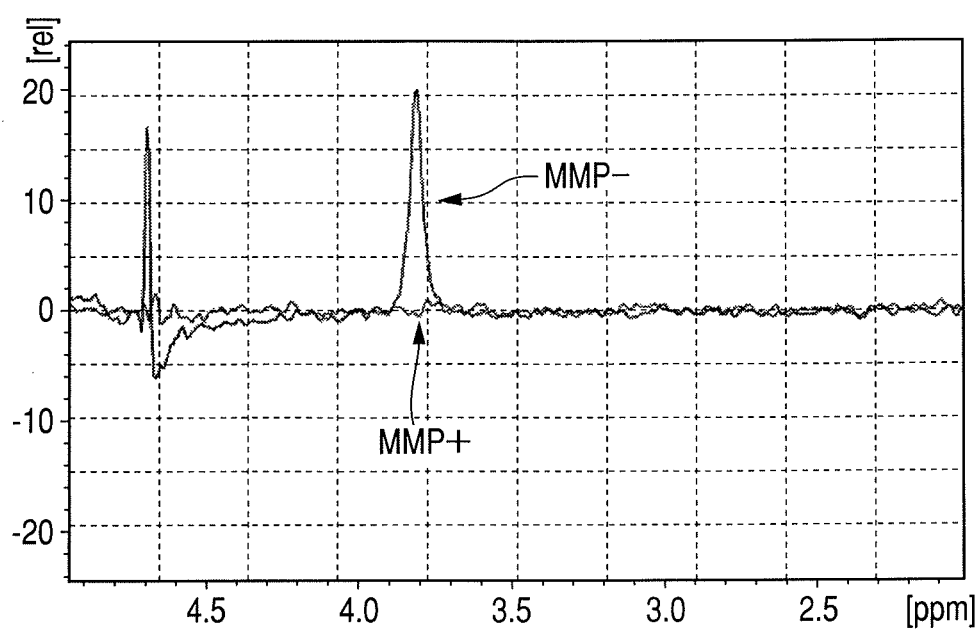
FIG. 9 shows proton NMR spectra of $^1H$—$^{13}C$—$^{13}C$-$^{15}N$ multi-dimensional resonance of the isotope-labeled peptide GPLGVRGK before the peptide (MMP−) is reacted with an enzyme and after the peptide (MMP+) is reacted with the enzyme.

FIG. 9 illustrates the proton NMR spectra of $^1$H—$^{13}$C—$^{13}$C—$^{15}$N multi-dimensional resonance of the isotope-labeled peptides (MMP−) and (MMP+) before and after the enzyme reaction. In this multi-dimensional resonance NMR observation method, to detect a bond of $^1$H—$^{13}$C—$^{13}$C—$^{15}$N, the peptide bond between glycine and valine at the enzyme cleavage site can be directly observed (since chemical shift of two $^{13}$C nuclei significantly differs, a fourth-dimensional resonance is said to occur in a strict sense). As is apparent from FIG. 9, a signal was detected at about 3.8 ppm in the spectrum (MMP−) before the enzyme reaction; however, this signal disappeared in the spectrum (MMP+) after the enzyme reaction.

Figure 10:
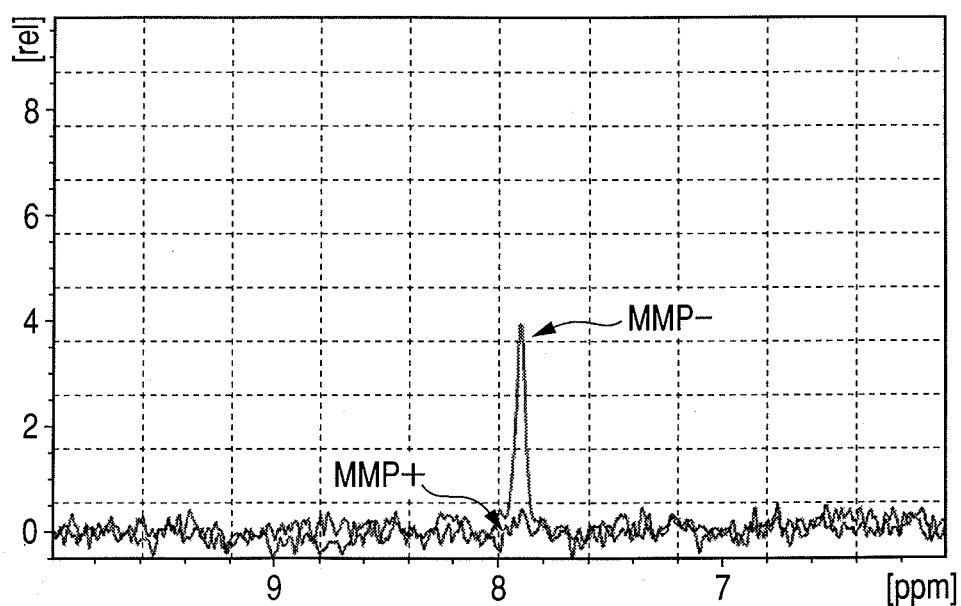
FIG. 10 shows proton NMR spectra of $^1H$-$^{15}N$-$^{13}C$ three-dimensional resonance of the isotope-labeled peptide GPLGVRGK before the peptide (MMP−) is reacted with an enzyme and after the peptide (MMP+) is reacted with the enzyme.

FIG. 10 illustrates the proton NMR spectra of $^1$H—$^{15}$N—$^{13}$C three-dimensional resonance of the isotope-labeled peptides (MMP−) and (MMP+) obtained before and after the enzyme reaction. In the observation method, since a bond of $^1$H—$^{15}$N—$^{13}$C was detected, the peptide bond between glycine and valine at the enzyme cleavage site can be directly observed. As is apparent from FIG. 10, the signal derived from an amide proton of valine was obtained at about 7.9 ppm in the spectrum (MMP−) before the enzyme reaction; however, the signal disappeared in the spectrum (MMP+) after the enzyme reaction.

The aforementioned results are summarized in Table 1.

TABLE 1

| | Time of Measurement for integration | MMP− (Before enzyme reaction) | MMP+ (After enzyme reaction) |
|---|---|---|---|
| $^1$H—$^{13}$C | 2 | 3.8 ppm | 3.6 ppm 3.7 ppm |
| $^1$H—$^{13}$C—$^{13}$C | 512 | — | 3.6 ppm 3.7 ppm |
| $^1$H—$^{13}$C—$^{13}$C—$^{15}$N | 512 | 3.8 ppm | — |
| $^1$H—$^{15}$N—$^{13}$C | 64 | 7.9 ppm | — |

—: Under the detection limit

The table shows chemical shift of a proton signal of two-dimensional NMR and multi-dimensional (three-dimensional or more) NMR of the isotope-labeled peptide GPLGVRGK before the peptide (MMP−) is reacted with an enzyme and after the peptide (MMP+) is reacted with the enzyme. Regardless of presence or absence of cleavage of the substrate peptide, $^1$H—$^{13}$C two-dimensional signal was observed. A multi-dimensional (three-dimensional or more) signal emerged or disappeared before and after the cleavage of the peptide.

As described above, the amount of a substrate peptide and the level of enzyme activity based on cleavage of the substrate peptide were able to be monitored by observing a two-dimensional resonance signal and a multi-dimensional (three dimensional or more) resonance signal.

Example 2

Multi-Dimensional Resonance NMR Analysis of Lactic Acid Production by Metabolic Reaction of Pyruvic Acid

Example 2-1

Experiment of Culturing HeLa Cells in a Medium Containing $^{13}$C-Labeled Pyruvic Acid $^{13}$C-labeled pyruvic acid was dissolved in a DMEM (+FBS) solution at 7 mM (30 ml) and the solution was sterilized by filtration. Three dishes were prepared in which a DMEM (+FBS) solution (9 ml) containing $^{13}$C-labeled pyruvic acid was poured. A DMEM (+FBS, +AB) solution (1 ml) containing Hela cells (700,000 cells/ml) was added to each of the dishes and cultured for 3 days under the conditions of 37° C., 5% CO$_2$.

After the culture solution was collected, each dish was washed with a PBS solution (3 ml). The washing solution was also collected together with the culture solution. Thereafter, a trypsin-EDTA solution (1.5 ml) was added and cells were removed from the dishes by a cell scraper. After that, this solution was collected in another tube. Washing was performed again by the PBS solution (3 ml) and collected together with a cell solution. The culture solution and cell solution thus collected were lyophilized. After the lyophilization, heavy water (3 ml) was added to the solid matter precipitated. The mixture was subjected to an ultrasonic treatment/centrifugation operation (5 min, 4500 rpm) and the supernatant was collected. The supernatant was further diluted to 10 fold with heavy water and subjected to multi-dimensional resonance NMR analysis.

Figure 11:
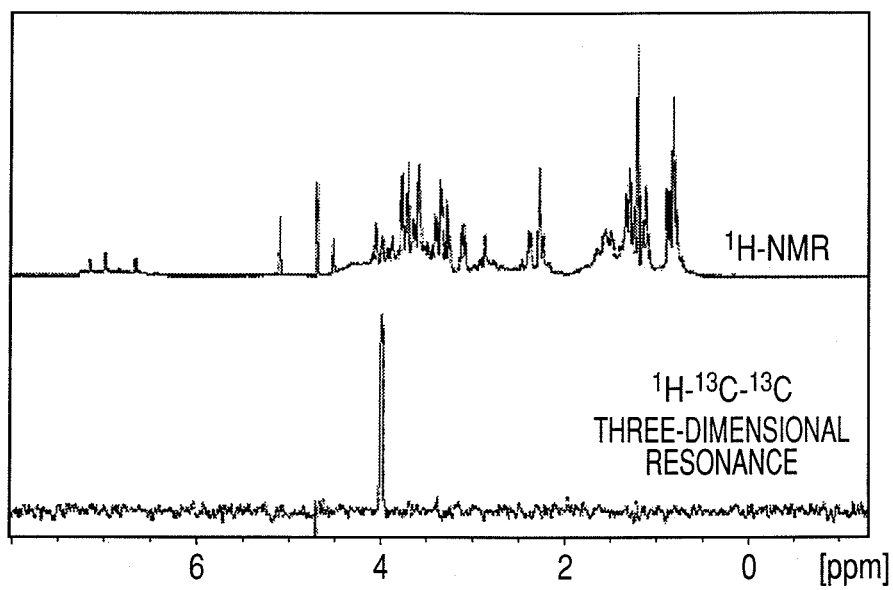
FIG. 11 shows spectra of $^1H$-NMR and $^1H$—$^{13}C$—$^{13}C$ three-dimensional NMR of a culture solution of HeLa cells cultured in a medium containing $^{13}C$-labeled pyruvic acid.
Figure 12:
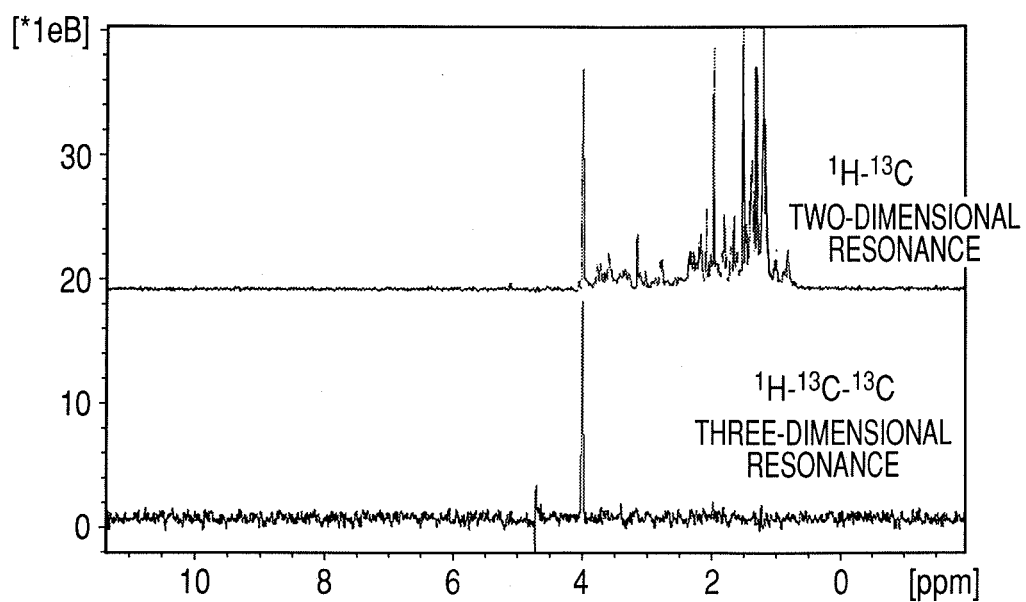
FIG. 12 shows spectra of $^1H$—$^{13}C$ two-dimensional NMR and $^1H$—$^{13}C$—$^{13}C$ three-dimensional NMR of a culture solution of HeLa cells cultured in a medium containing $^{13}C$-labeled pyruvic acid.
Figure 13:
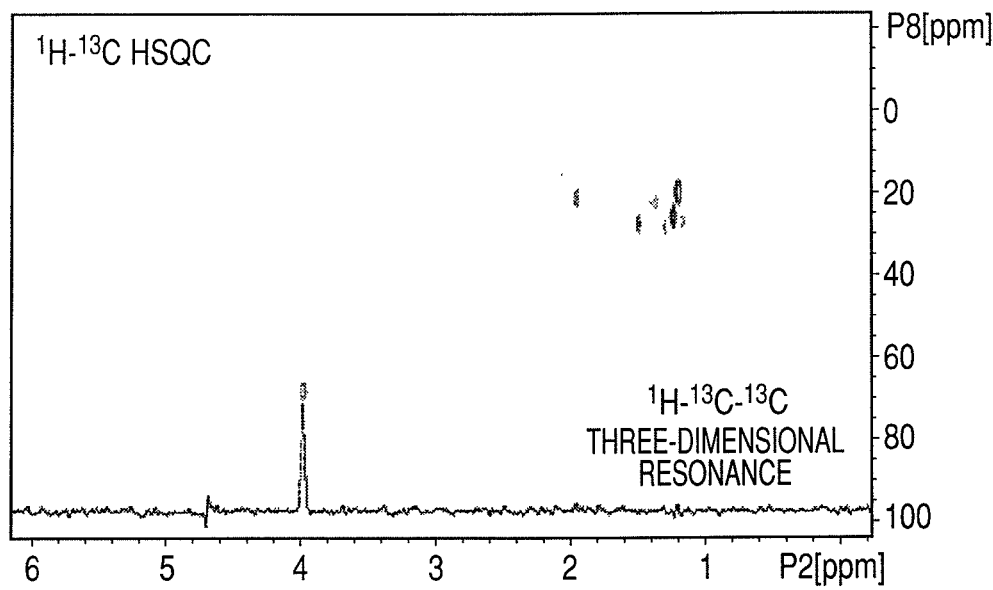
FIG. 13 shows a spectrum of $^1H$—$^{13}C$—$^{13}C$ three-dimensional NMR and $^1H$—$^{13}C$ HSQC spectrum of a culture solution HeLa cells cultured in a medium containing $^{13}C$-labeled pyruvic acid.
Figure 14:
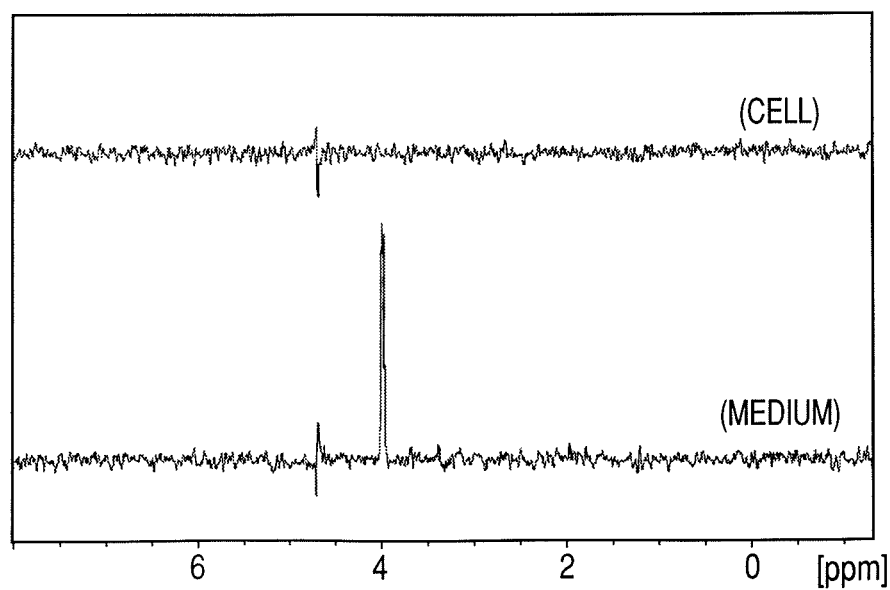
FIG. 14 shows spectra of $^1H$—$^{13}C$—$^{13}C$ three-dimensional NMR of a culture solution of HeLa cells cultured in a medium containing $^{13}C$-labeled pyruvic acid and of the HeLa cells.

FIG. 11 shows the measurement results of multi-dimensional resonance NMR of the culture solution. Many peaks derived from components of the culture were detected in $^1$H-NMR, whereas only a signal from the methine proton of lactic acid was detected at 4.0 ppm in $^1$H—$^{13}$C—$^{13}$C three-dimensional resonance. A signal from methyl proton of pyruvic acid was not detected. FIG. 12 shows measurement of $^1$H—$^{13}$C two-dimensional resonance and $^1$H—$^{13}$C—$^{13}$C three-dimensional resonance of the culture solution. Many signals that may be derived from components of the culture were detected in the two-dimensional resonance, whereas only a signal derived from lactic acid produced from labeled pyruvic acid in the three-dimensional resonance was detected. FIG. 13 shows the measurement results of three-dimensional resonance and $^1$H—$^{13}$C HSQC of the culture solution. The $^1$H signal at 4.0 ppm detected in the $^1$H—$^{13}$C—$^{13}$ three-dimensional resonance is the $^1$H bound to $^{13}$C having a peak at about 60 ppm. From this, the $^1$H signal is conceivably derived from the methine proton of lactic acid. FIG. 14 shows measurement results of $^1$H—$^{13}$C—$^{13}$C three-dimensional resonance NMR of the culture solution and cells. Nothing was detected in the system of cells. A signal from the methyl proton of pyruvic acid was detected in neither of them and a signal from lactic acid was detected only in the medium. From this, it is considered that the labeled pyruvic acid administered was all consumed. In addition, the data indicated that the labeled pyruvic acids were metabolized into lactic acids by lactic dehydrogenase derived from cells.

Example 2-2

Multi-Dimensional Resonance Measurement of $^{13}$C-Labeled Pyruvic Acid-Containing Medium Without HeLa Cells Next, as a negative control test, the measurement was performed without (in the absence of) Hela cells in the same conditions as above in order to confirm that lactic acid is a metabolite by lactic dehydrogenase derived from Hela cells. $^{13}$C-labeled pyruvic acid was dissolved in a DMEM (+FBS) solution, controlled to obtain a 7 mM solution (10 ml) and sterilized by filtration. A single dish was prepared in which a DMEM (+FBS) solution (9 ml) containing $^{13}$C-labeled pyruvic acid was poured. To this, a DMEM (+FBS, +AB) solution (1 ml) containing no HeLa cells was added and cultured for 3 days under the conditions of 37° C., 5% $CO_2$. After the culture solution was collected, the dish was washed with a PBS solution (3 ml). The washing solution was also collected together with the culture solution. The culture solution collected was lyophilized. After the lyophilization, heavy water (1 ml) was added to the solid matter precipitated. The mixture was subjected to an ultrasonic treatment/centrifugation operation (5 min, 4500 rpm) and the supernatant (50 μl) was collected. The supernatant (50 μl) was further diluted to 10 fold with heavy water and subjected to multi-dimensional resonance NMR analysis.

Figure 15:
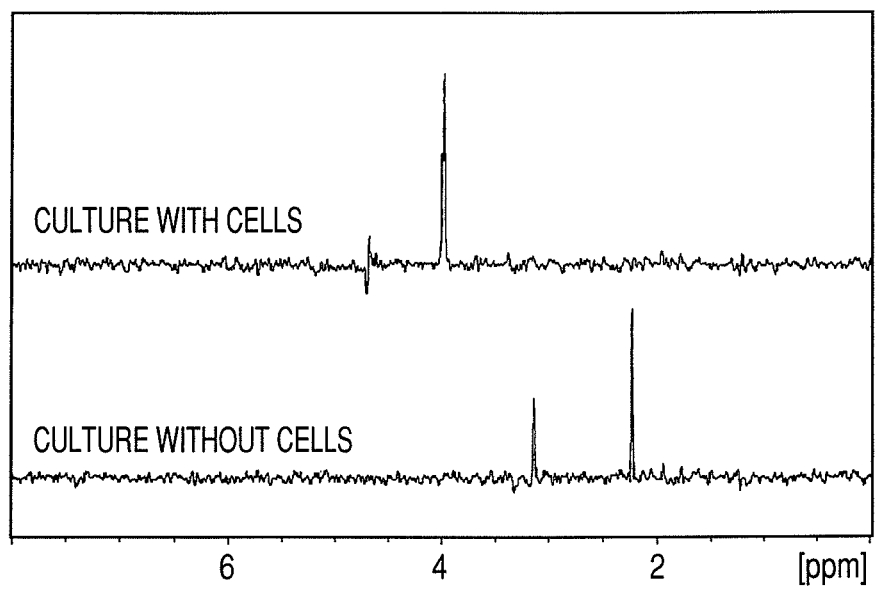
FIG. 15 shows spectra of $^1H$—$^{13}C$—$^{13}C$ three-dimensional NMR of a culture solution of the culture performed without cells (a negative control test) and a culture solution of the culture performed in the presence of HeLa cells.

FIG. 15 shows the measurement results of $^1$H—$^{13}$C—$^{13}$C three-dimensional resonance of the negative control test (blue) performed without cells and a HeLa cell culture test (red). In the case of culturing without cells, no peak derived from lactic acid was detected and a peak (about 2.2 ppm) derived from the methyl proton of pyruvic acid was detected. From this, it was found that pyruvic acid is metabolized into lactic acid. From the results mentioned above, it was demonstrated that the metabolic reaction from 13C-labeled pyruvic acid into lactic acid by lactic dehydrogenase derived from a cell could be detected with high contrast by three-dimensional resonance measurement.

Example 3

Selective Detection of Glycolytic Reaction Using an Isotope-Labeled Glucose ($^{13}C_6$, $^2H_7$-D-glucose))

Example 3-1

Preparation of Cancer-Bearing Mouse

From a dish having colon-26 cells cultured therein, medium was removed. After the dish was washed with PBS, trypsin (5 ml) was added to separate the cells. Medium was added to the cell suspension solution and the mixture was transferred to a tube and centrifugally separated to precipitate the cells. Thereafter, the supernatant was removed and the cells were dissolved in PBS (10 ml). The cells were counted and the number of cells was adjusted to $4.0 \times 10^7$ cells/ml. A colon-26 cell solution (100 μl) was subcutaneously administered to the left leg of BALB/c mouse. The mouse was kept under fasting condition for 1 day.

Example 3-2

Administration of $^{13}C_6$, $^2H_7$-D-Glucose, Anatomy and NMR Analysis

A PBS solution (200 μl) of $^{13}C_6$, $^2H_7$-D-glucose was administered to the tail vein of a cancer-bearing mouse in a dose of 5 g/kg per weight of the mouse. One hour later, the mouse was cut out and necessary organs (blood (200 μl), liver, kidney, cancer site, heart) were successively taken out. The tissues except the blood were washed with physiological saline and separately collected in Eppendorf tubes. To each of the tubes, 10% trichloroacetic acid (500 μl) was added. Each organ was mashed by use of beads and then incubated on ice for 30 minutes. After insoluble matter was precipitated by centrifugation (4° C., 12000 rpm, 5 min), the supernatant was collected. Again, 10% trichloroacetic acid (200 μl) was added to the precipitate and centrifuged (4° C., 12000 rpm, 5 min). Thereafter, the supernatant was also collected and all supernatants were lyophilized. To the lyophilized extract from the cancer site, heavy water (700 μl) was added and then, multi-dimensional resonance NMR analysis was performed.

Figure 16:
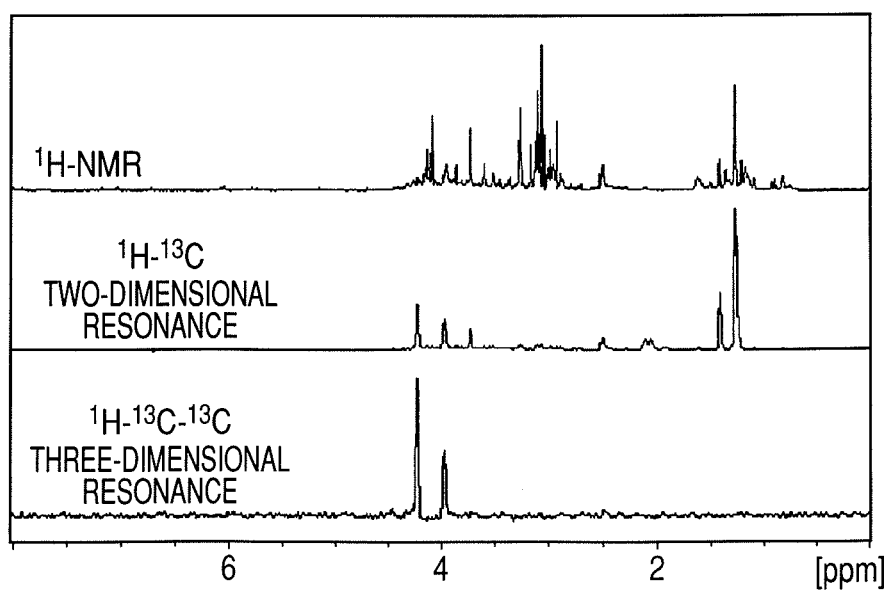
FIG. 16 shows NMR spectra of a cancer site of a cancer-bearing mouse administered with $^{13}C_6$, $^2D_7$-D-glucose.
Figure 17:
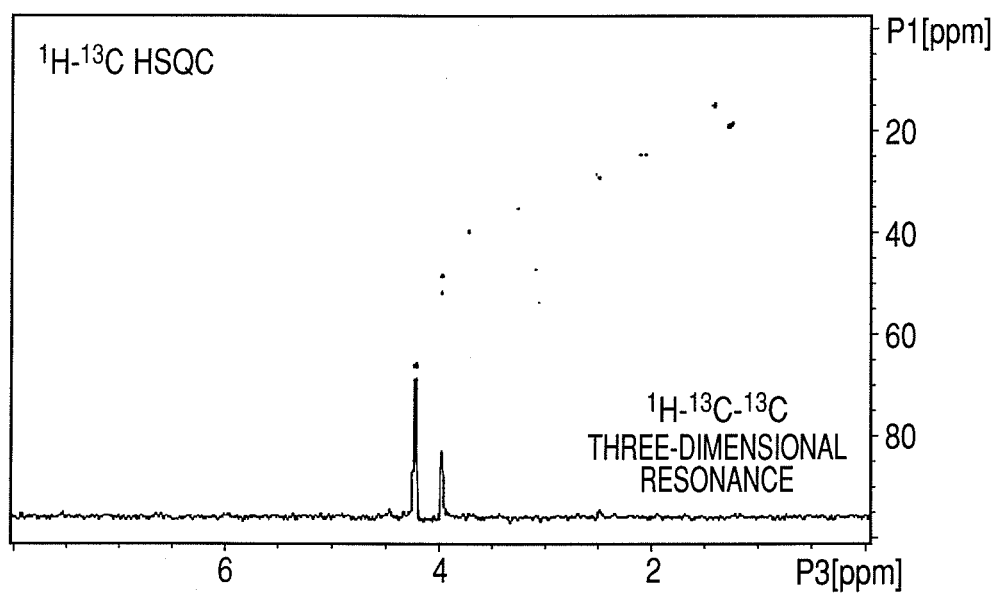
FIG. 17 shows a spectrum of $^1H$—$^{13}C$—$^{13}C$ three-dimensional NMR and an $^1H$—$^{13}C$ HSQC spectrum of a cancer site of a cancer-bearing mouse administered with $^{13}C_6$, $^2D_7$-D-glucose.

FIG. 16 shows the NMR measurement results of the cancer site of the cancer-bearing mouse one hour after administration of $^{13}C_6$, $^2H_7$-D-glucose. In the $^1$H-NMR, many signals derived from endogenous substances were detected. In the $^1$H—$^{13}$C two-dimensional resonance, a plurality of signals were detected although many signals did not appear. In the $^1$H—$^{13}$C—$^{13}$C three-dimensional resonance, two signals alone were detected. It is estimated that one of them is a signal from lactic acid and the other is a signal from alanine. FIG. 17 shows the NMR measurement results of $^1$H—$^{13}$C—$^{13}$C three-dimensional resonance NMR of the cancer site in comparison with the measurement results of $^1$H—$^{13}$C HSQC. A signal (at 4.2 ppm) from $^1$H, which is bound to carbon $^{13}$C having a peak at about 67 ppm, is found to be derived from the methine proton of lactic acid. It is found that the signal from $^1$H at 4.0 ppm is derived from alanine $^1$H—$^{13}$C—$^{13}$C since $^{13}$C signal appears at about 50 ppm. From the results mentioned above, it was demonstrated that the final stage of the glycolytic reaction can be selectively detected by the three-dimensional resonance analysis using $^{13}C_6$, $^2H_7$-D-glucose.

Figure 18:
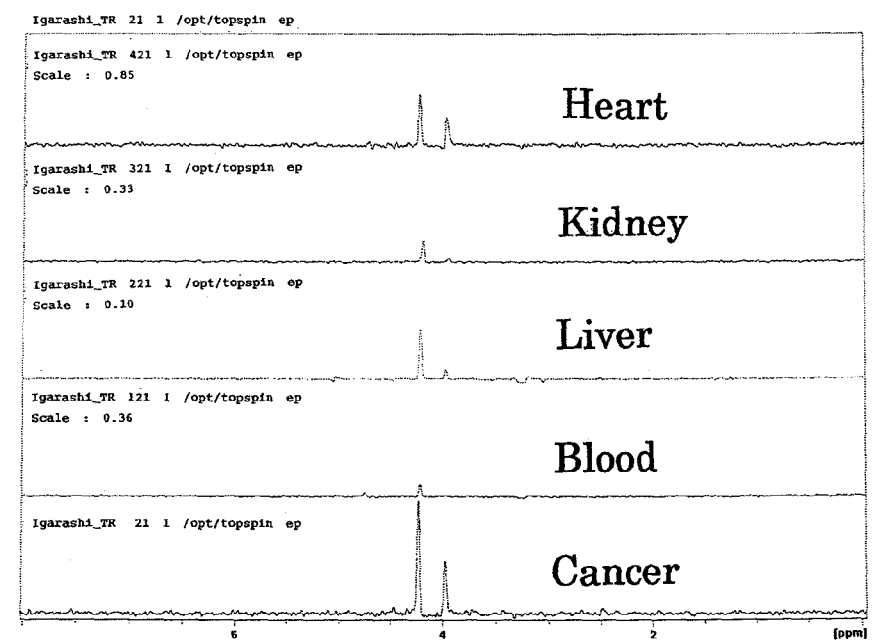
FIG. 18 shows spectra of $^1H$—$^{13}C$—$^{13}C$ three-dimensional NMR of heart, kidney, liver, blood, and cancer site of a cancer-bearing mouse administered with $^{13}C_6$, $^2D_7$-D-glucose (5 g/kg mouse weight).

FIG. 18 shows the NMR measurement results of $^1$H-$^{13}$C—$^{13}$C three-dimensional resonance NMR of the heart, kidney, liver, blood, and cancer site in an administration dose of 5 g/kg. The signal intensity is normalized using weight of each organ, i.e. signal intensity per organ weight. The highest intensity in the cancer site demonstrates that the labeled glucoses are accumulated specifically in the cancer site. Especially, the alanine signals in blood, kidney, and liver were significantly low, which demonstrated the signal detection with high specificity in the cancer site using the labeled glucose probe.

Figure 19:
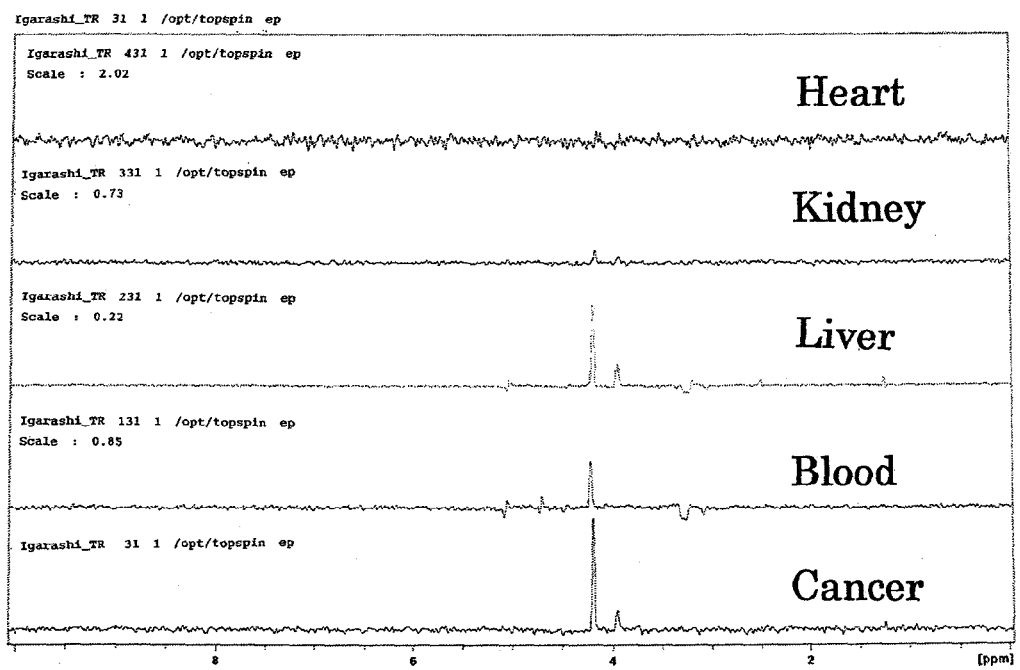
FIG. 19 shows spectra of $^1H$—$^{13}C$—$^{13}C$ three-dimensional NMR of heart, kidney, liver, blood, and cancer site of a cancer-bearing mouse administered with $^{13}C_6$, $^2D_7$-D-glucose (3 g/kg mouse weight).

FIG. 19 shows the NMR measurement results of $^1$H-$^{13}$C—$^{13}$C three-dimensional resonance NMR of the heart, kidney, liver, blood, and cancer site in an administration dose of 3 g/kg. The signal intensity is normalized using weight of each organ. The highest signal intensity from the lactic acid was detected in the cancer site. The alanine signal was not detected in the heart.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2007-232665, filed Sep. 7, 2007 and 2008-228433, filed Sep. 5, 2008, which are hereby incorporated by reference in its entirety.

The invention claimed is:

1. A substrate probe for use in measuring enzyme activity by using a three-dimensional nuclear magnetic resonance method,
    wherein the probe has an enzyme recognition site, which is selectively recognized by an active-state enzyme, and
    wherein a first nuclear magnetic resonance active nuclei having a nuclear spin, a second nuclear magnetic resonance active nuclei having a nuclear spin, and a third nuclear magnetic resonance active nuclei having a nuclear spin are present in the enzyme recognition site,
    wherein the second nuclear magnetic resonance active nuclei is connected to the first nuclear magnetic resonance active nuclei and the third nuclear magnetic resonance active nuclei is connected to the second nuclear magnetic resonance active nuclei,
    wherein each of the first, second, and third nuclear magnetic resonance active nuclei has a different resonance frequency,
    wherein the probe is pyruvic acid or a salt thereof, and
    wherein a carbon at a 2-position and a carbon at a 3 position of the pyruvic acid or the salt thereof are labeled with $^{13}$C and a hydrogen atom bound with the carbon of the 3-position of the pyruvic acid or the salt thereof is deuterated.

2. A substrate probe for use in measuring enzyme activity by using a three-dimensional nuclear magnetic resonance method,
    wherein the probe has an enzyme recognition site, which is selectively recognized by an active-state enzyme,
    wherein a first nuclear magnetic resonance active nuclei having a nuclear spin, a second nuclear magnetic resonance active nuclei having a nuclear spin, and a third nuclear magnetic resonance active nuclei having a nuclear spin are present in the enzyme recognition site,
    wherein the second nuclear magnetic resonance active nuclei is connected to the first nuclear magnetic resonance active nuclei and the third nuclear magnetic resonance active nuclei is connected to the second nuclear magnetic resonance active nuclei,
    wherein each of the first, second, and third nuclear magnetic resonance active nuclei has a different resonance frequency,
    wherein the substrate probe is glucose, and
    wherein all carbons of 1 to 6 positions of the glucose are labeled with 13C and 7 hydrogen atoms that bind with the carbon of the 1 to 6 positions thereof are all deuterated.

3. The substrate probe according to claim 1, wherein the enzyme is a glycolytic enzyme.

4. The substrate probe according to claim 3, wherein the glycolytic enzyme is lactic dehydrogenase.

5. A substrate probe for nuclear magnetic resonance imaging comprising the substrate probe according to claim 1, for detecting abnormal enzyme activity involved in a disease.

6. The substrate probe according to claim 1, for detecting a glycolytic metabolite, lactic acid.

7. A substrate peptide-probe for use in measuring protease activity by a three-dimensional nuclear magnetic resonance method,
    wherein the probe has a protease cleavage site that is selectively recognized and cleaved by an active-state protease,
    wherein a first nuclear magnetic resonance active nuclei having a nuclear spin, a second nuclear magnetic resonance active nuclei having a nuclear spin, and a third nuclear magnetic resonance active nuclei having a nuclear spin are present in the protease cleavage site,
    wherein the second nuclear magnetic resonance active nuclei is connected to the first nuclear magnetic resonance active nuclei and the third nuclear magnetic resonance active nuclei is connected to the second nuclear magnetic resonance active nuclei, wherein each of the first, second, and third nuclear magnetic resonance active nuclei has a different resonance frequency, wherein the substrate peptide-probe is an oligopeptide having a structure represented by general formula (I):

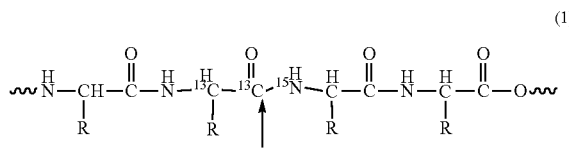
(1)

where Rs represent amino acid side-chains that may be mutually different and the arrow indicates a protease cleavage site, and wherein an amino acid residue at the protease cleavage site closer to an N terminal has an amino acid skeleton in which 1-position and 2-position carbon atoms are labeled with $^{13}C$, and an amino acid residue at the protease cleavage site closer to a C terminal has an amino acid skeleton in which a nitrogen atom is labeled with $^{15}N$.

8. The substrate peptide-probe according to claim 7, wherein an amino acid sequence of the substrate peptide is SEQ ID NO:1 and a 4th amino acid (Gly) from the N terminal has an amino acid skeleton whose 1-position and the 2-position carbon atoms are labeled with $^{13}C$ and a 5th amino acid (Val) from the N terminal has an amino acid skeleton whose nitrogen atom is labeled with $^{15}N$.

9. The substrate peptide-probe according to claim 7, wherein the protease is matrix metalloprotease (MMP).

10. The substrate peptide-probe according to claim 8, wherein the protease is matrix metalloprotease 2 (MMP 2).

11. A substrate peptide-probe for use in nuclear magnetic resonance imaging, comprising the substrate peptide-probe according to claim 7, for detecting abnormal protease activity involved in a disease.

12. The substrate probe according to claim 1, wherein the probe has a structure represented by general formula (7):

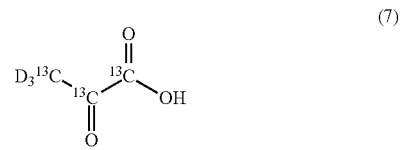
(7)

13. The substrate probe according to claim 7, wherein the probe has a structure represented by general formula (8):

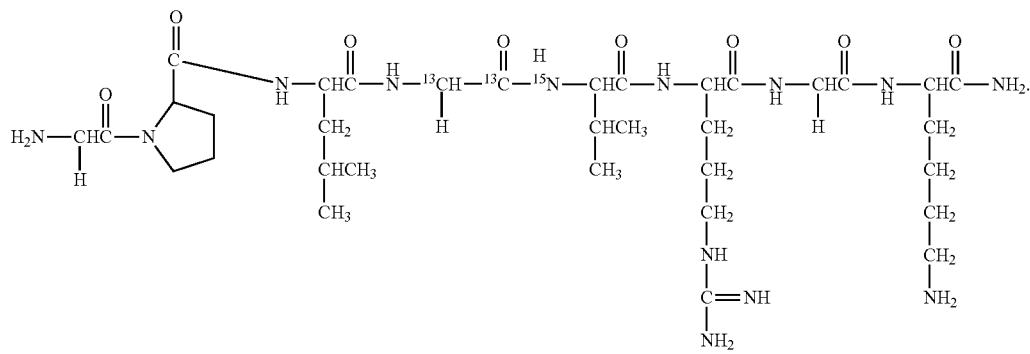

* * * * *

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Probe

<400> SEQUENCE: 1

Gly Pro Leu Gly Val Arg Leu Lys
1               5
```